United States Patent [19]

Chou

[11] 4,289,695

[45] Sep. 15, 1981

[54] PROCESS FOR PREPARING 2-CHLOROSULFINYLAZETIDINONES

[75] Inventor: Ta-Sen Chou, Indianapolis, Ind.

[73] Assignee: Eli Lilly and Company, Indianapolis, Ind.

[21] Appl. No.: 49,266

[22] Filed: Jun. 18, 1979

Related U.S. Application Data

[63] Continuation-in-part of Ser. No. 960,347, Nov. 13, 1978, abandoned.

[51] Int. Cl.$^3$ .................. C07D 205/08; C07D 405/12; C07D 409/12
[52] U.S. Cl. .............................. 260/239 A; 260/330.3; 260/347.4
[58] Field of Search .................. 260/332.2 H, 347.4, 260/239 A, 330.3

[56] References Cited

U.S. PATENT DOCUMENTS

| | | | |
|---|---|---|---|
| 4,075,203 | 2/1978 | Chon | 544/18 |
| 4,081,440 | 3/1978 | Kakolja | 260/239 A |
| 4,159,272 | 6/1979 | Chou | 260/239 A |

OTHER PUBLICATIONS

Hallensleber et al., Ang. Chem. Int. Ed. 15, 163, (1976).

*Primary Examiner*—Mark L. Berch
*Attorney, Agent, or Firm*—William B. Scanlon; Arthur R. Whale

[57] ABSTRACT

Improved process for converting a penicillin sulfoxide ester to a 2-chlorosulfinylazetidin-4-one intermediate which on cyclization affords a 3-exomethylenecepham sulfoxide, wherein the penicillin sulfoxide ester is reacted with an N-chloro halogenating agent in the presence of a cross-linked polyvinylpyridine polymer to provide the 2-chlorosulfinylazetidin-4-one.

16 Claims, No Drawings

PROCESS FOR PREPARING 2-CHLOROSULFINYLAZETIDINONES

CROSS-REFERENCE TO RELATED APPLICATION

This application is a continuation-in-part of application Ser. No. 960,347 filed Nov. 13, 1978 now abandoned.

SUMMARY OF THE INVENTION

This invention relates to an improved process for the preparation of 2-chlorosulfinylazetidin-4-ones with penicillin sulfoxide esters. In particular, it relates to an improvement in the first step of a two-step process for converting a penicillin sulfoxide ester via a 2-chlorosulfinylazetidin-4-one intermediate to a 3-exomethylenecepham sulfoxide. In one aspect of this invention, a penicillin sulfoxide ester is reacted with an N-chloro halogenating agent at a temperature of from about 75° C. to about 175° C. in the presence of the weakly basic, organic solvent insoluble, cross-linked polyvinylpyridine polymer to provide a 2-chlorosulfinylazetidin-4-one. The vinylpyridine copolymer effects the rapid removal of hydrogen chloride from the heterogenous reaction medium, and thus prevents the development of side products. Further, the vinylpyridine cross-linked polymer with bound acid is readily removed from the reaction medium by filtration or other suitable means.

The 2-chlorosulfinylazetidin-4-ones are useful intermediates in the process described by Kukolja (U.S. Pat. No. 4,052,387) for the preparation of 3-exomethylenecepham-4-carboxylic acid ester sulfoxides. The improved process of this invention and the cyclization of the 2-chlorosulfinylazetidinones are illustrated in the following reaction scheme.

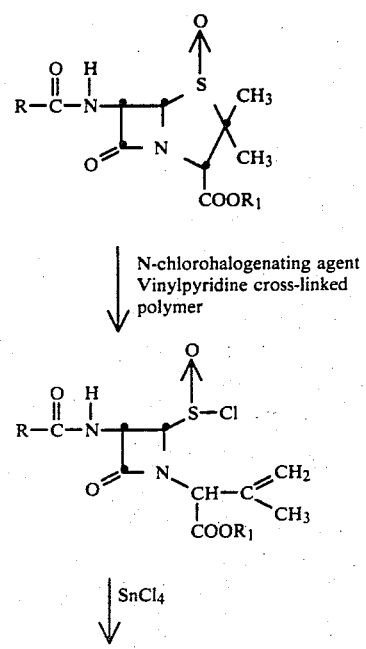

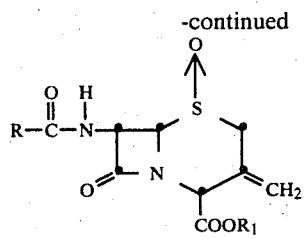

In the foregoing reaction scheme, R represents an organic radical, for example, benzyl or phenoxymethyl, and $R_1$ represents a carboxylic acid protecting group. The sulfoxide of the penicillin sulfoxide ester employed as starting material can have either the α or β configuration (R or S).

BACKGROUND OF THE INVENTION

The 2-chlorosulfinylazetidin-4-one compounds produced as intermediates in the improved process of this invention as well as like compounds have been previously described. In U.S. Pat. No. 3,960,851, June 1, 1976, Kukolja et al. describe 3-imido substituted 2-chlorosulfinylazetidin-4-ones, wherein the amino group of the azetidinone is diacylated with a derivative of a dicarboxylic acid, and the conversion of the 3-imido azetidinones to 3-methyl-3-cephems (desacetoxycephalosporins). In U.S. Pat. No. 3,843,682, Oct. 22, 1974, Kukolja et al. also disclose 3-imido-2-chlorosulfinylazetidin-4-ones. Subsequently, Kukolja in U.S. Pat. No. 4,081,440, Mar. 28, 1978, discloses 3-amido-2-chlorosulfinylazetidin-4-one compounds wherein the 3-amino group of the azetidinone is monoacylated. There is also disclosed a process for preparing the 3-amidoazetidinones via treatment of a penicillin sulfoxide ester with an N-chloro halogenating agent.

In U.S. Pat. No. 4,052,387, Oct. 4, 1977, Kukolja discloses a method for the preparation of 3-exomethylenecepham sulfoxides by cyclizing the 3-amido-2-chlorosulfinylazetidin-4-ones with a Friedel-Crafts catalyst or a metathetic cation-forming agent.

Further, Ta-Sen Chou discloses in U.S. Pat. No. 4,075,203, February 21, 1978, an improved process for preparing a 3-exomethylenecepham compound which comprises the use of an alkylene oxide in combination with calcium oxide in the 3-amido-2-chlorosulfinylazetidin-4-one forming step of the overall process.

This invention provides yet a further improvement in the two-step process for preparing 3-exomethylenecepham sulfoxides with penicillin sulfoxide esters via the intermediate 2-chlorosulfinylazetidin-4-ones. The improvement of this invention comprises utilizing in the first step of the process a weakly basic, organic solvent insoluble polymer of polyvinylpyridine cross-linked with e.g. divinylbenzene as the hydrogen chloride acceptor, in the formation of the intermediate 2-chlorosulfinylazetidin-4-one.

The 3-exomethylenecepham sulfoxides are valuable intermediates for cephalosporin antibiotic compounds. For example, they can be converted by ozonolysis of the 3-exomethylene group to 3-hydroxy-3-cephem ester sulfoxides. The latter can be halogenated to provide the corresponding 3-halo-3-cephem esters or the intermediate 3-hydroxy compound can be reacted with a diazoalkane, for example, diazomethane, to provide the corresponding 3-methoxy-3-cephem ester sulfoxide. The sulfoxide form of these compounds can be reduced by known methods, for example, the method described by Murphy et al. in U.S. Pat. No. 3,641,014, Feb. 8, 1972, but especially that described by Hatfield in U.S. Pat. No. 4,044,002, Aug. 23, 1977. Deesterification of the intermediate 3-halo or 3-methoxy esters affords antibiotic compounds. For example, 3-methoxy substituted cephalosporin antibiotics are described by Chauvette in U.S. Pat. No. 3,917,587 and 3,917,588, while Chauvette also describes 3-halo substituted cephalosporin antibiotics in U.S. Pat. Nos. 4,064,343, 3,962,227, and 3,925,372.

DETAILED DESCRIPTION

According to the process of this invention, a 6-acylamido-2,2-dimethylpenam-4-carboxylic acid ester sulfoxide represented by the following formula 1,

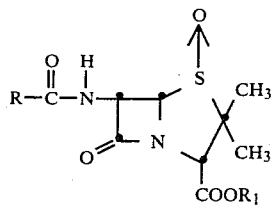

wherein R represents the residue of a carboxylic acid and $R_1$ represents a carboxylic acid protecting group, is reacted in an inert organic solvent at a temperature between about 75° C. to about 175° C. and preferably between about 110° C. and about 155° C. under essentially anhydrous conditions with an N-chloro halogenating agent in the presence of a cross-linked polyvinylpyridine polymer to form the correspondingly substituted 2-chlorosulfinylazetidin-4-one represented by the following formula 2.

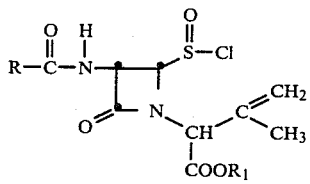

The insoluble copolymer is filtered from the reaction mixture and the 2-chlorosulfinylazetidinone is isolated or, alternatively the filtrate is treated with a Friedel-Crafts catalyst to effect cyclization of the 2-chlorosulfinylazetidine to the 3-exomethylenecepham.

The penicillin sulfoxide starting material can have either the α or the β configuration (R or S). The preparation of penicillin sulfoxides is well known in the art, for example, the penicillin β-sulfoxides can be prepared by reacting the penicillin with organic peracids such as perbenzoic acid, peracetic acid, or preferably m-chloroperbenzoic acid or with an inorganic oxidizing agent such as with sodium periodate. Penicillin α-sulfoxides are preferably prepared by reacting the penicillin with ozone in an inert solvent and thereafter separating the mixture of α- and β-sulfoxides formed. The preparation of penicillin α-sulfoxides with ozone is described by Spry in U.S. Pat. No. 3,691,188.

As mentioned above, the reaction of a penicillin sulfoxide ester with an N-chloro halogenating agent is carried out in an inert organic solvent under essentially anhydrous conditions. The term "inert organic solvent" refers to an aprotic organic solvent which under the conditions of the process disclosed herein does not react appreciably with either the N-chlorinating agent or the 2-chlorosulfinylazetidinone. Suitable inert organic solvents are those having a boiling point at least as high as the temperature of reaction and include the aromatic hydrocarbons such as benzene, toluene, ethylbenzene, cumene, the xylenes, tetralin, and the like; the halogenated hydrocarbons such as carbon tetrachloride, chloroform, 1,1,2-trichloroethane, ethylene dibromide, and like halogenated hydrocarbon solvents; and aromatic ethers such as anisole, phenetole, diphenylether and the like. Preferred organic solvents of this process are benzene, toluene, and the xylenes. Reagent grade solvents are preferably used and are suitably dried, for example, by binary distillation or, alternatively, with a molecular sieve, or with one of the conventional drying agents such as calcium chloride, magnesium sulfate, sodium sulfate, and the like.

The temperature at which the process is carried out can be increased with a given solvent, e.g. benzene or toluene, by carrying out the process at an elevated pressure e.g., at about 10 psig to about 25 psig.

The N-chloro halogenating agents employed in the process of this invention are represented by the following structural formula.

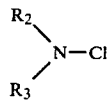

wherein $R_2$ is hydrogen, chloro, $C_1$-$C_3$ alkyl, cyclohexyl, phenyl, or phenyl substituted with chloro, bromo, methyl, or nitro, and $R_3$ is $R_4$—X— wherein $R_4$ is $C_1$-$C_3$ alkyl, cyclohexyl, phenyl, or phenyl substituted with chloro, bromo, methyl, or nitro, and X

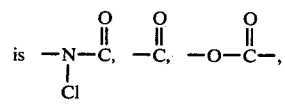

or —$SO_2$—; or $R_2$ and $R_3$ taken together with the nitrogen to which they are bonded define a heterocyclic structure of the formula

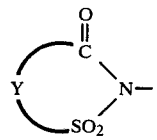

in which Y is o-phenylene or —$(CH_2)_n$— in which n is 2 or 3; or a structure of the formula

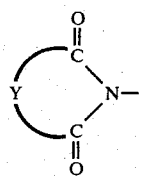

in which Y is as hereinbefore defined.

Several types of preferred N-chloro compounds which can be employed in producing the sulfinyl chlorides are described by the above definition. These N- chloro compounds include (a) ureas, (b) amides, (c) urethans, (d) sulfonamides, (e) sulfimides, and (f) imides.

The preferred N-chloro ureas which can be employed in this invention generally have the formula

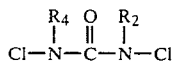

in which $R_2$ is hydrogen, chloro, $C_1$–$C_3$ alkyl, cyclohexyl, phenyl, or phenyl substituted with chloro, bromo, methyl, or nitro, and $R_4$ is $C_1$–$C_3$ alkyl, cyclohexyl, phenyl, or phenyl substituted with chloro, bromo, methyl, or nitro.

Illustrative of these ureas are
N,N'-dichloro-N-methylurea;
N,N'-dichloro-N-ethyl-N'-cyclohexylurea;
N,N'-dichloro-N-phenylurea;
N,N'-dichloro-N,N'-diphenylurea;
N,N'-dichloro-N-(p-tolyl)urea;
N,N'-dichloro-N-(m-chlorophenyl)-N'-methylurea;
N,N'-dichloro-N,N'-dicyclohexylurea;
N,N'-dichloro-N-isopropyl-N'-(p-tolyl)urea;
N,N'-dichloro-N-phenyl-N'-propylurea;
N,N'-dichloro-N-cyclohexyl-N'-(p-nitrophenyl)urea;
N,N,N'-trichloro-N-methylurea;
N,N,N'-trichloro-N-phenylurea; and the like.

The preferred N-chloro amides which can be employed in this invention generally have the formula

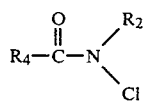

in which $R_2$ and $R_4$ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)-butyramide, N-chlorohexahydrobenzamide, N,2,4-trichloroacetanilide, and the like.

The preferred N-chloro urethans which can be used in preparation of the sulfinyl chlorides in accordance with this invention generally have the formula

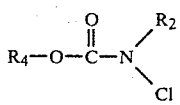

in which $R_2$ and $R_4$ are as hereinbefore defined.

Illustrative of these urethanes are methyl N,N-dichlorocarbamate, ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorophenyl N-methyl-N-chlorocarbamate, cyclohexyl N-cyclohexyl-N-chlorocarbamate, isopropyl N-p-tolyl-N-chlorocarbamate, phenyl N-propyl-N-chlorocarbamate, cyclohexyl N-p-nitrophenyl-N-chlorocarbamate, and the like.

Preferred N-chloro sulfonamides which can be used to prepare the sulfinyl chlorides in accordance with this invention have the formula

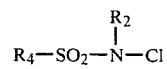

in which $R_2$ and $R_4$ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorobenzenesulfonamide, N-methyl-N-chloro-p-toluenesulfonamide, N-cyclohexyl-N-chlorocyclohexanesulfonamide, N-p-tolyl-N-chlorisopropanesulfonamide, N-propyl-N-chlorobenzenesulfonamide, N-p-nitrophenyl-N-chlorocyclohexanesulfonamide, and the like.

A further preferred type of N-chloro halogenating agent which can be employed in the preparation of the sulfinyl chlorides is a sulfimide of the formula

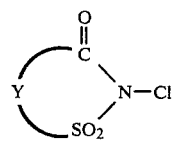

in which Y is o-phenylene, —$CH_2$—$CH_2$—, or —$CH_2$—$CH_2$—$CH_2$—. These compounds include o-sulfobenzoic N-chloroimide, β-sulfopropionic N-chloroimide, and γ-sulfobutyric N-chloroimide.

Especially preferred for use as N-chlorohalogenating agents in the preparation of the sulfinyl chlorides in accordance with this invention are N-chloroimides of the formula

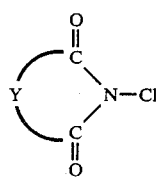

in which Y is o-phenylene, —$CH_2$—$CH_2$—, or —$CH_2$—$CH_2$—$CH_2$—. These compounds include N-chlorophthalimide, N-chlorosuccinimide, and N-chloroglutarimide.

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., *J. Org. Chem.* 39, (1974) pp. 3136–3138; Theilacker et al., *Liebigs Ann. Chem.* 703, (1967) pp. 34–36; and Houben-Weyl, *Methoden der Organischem Chemie*, Volume V/3, pp. 796–810.

N-Chloro halogenating agents which are preferred for use in the process of this invention are N-chloro imides, particularly N-chlorosuccinimide or N-chlorophthalimide, and, especially N-chlorophthalimide.

The cross-linked polyvinylpyridine polymers employed in the process of this invention are weakly basic resins which are insoluble in the inert organic solvents and, in particular, the reaction medium employed in the present process. The polymers contain cross-linking of from about 1% to about 10%.

The cross-linked polyvinylpyridine polymer is prepared by polymerizing vinylpyridine monomer in the presence of the cross-linking agent. The term "vinylpyridine" is used herein to mean 4-vinylpyridine, 3-vinylpyridine, 2-vinylpyridine and the methylated vinylpyridines such as 2-methyl-4-vinylpyridine and 3-methyl-4-vinylpyridine. 4-Vinylpyridine is the preferred monomer. The polyvinylpyridines can be cross-linked with a wide variety of known crosslinking agents. Examples of cross-linking agents are the difunctional agents such as vinyl aromatics, for example, divinylbenzene, the acrylamides such as N,N'-methylenebisacrylamide

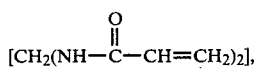

and N,N'-decamethylenebisacrylamide, and N,N-diallylacrylamide; the acrylate and methylacrylate esters such as ethylene diacrylate, ethylene dimethylacrylate, and triethyleneglycol dimethacrylate; the allyl esters of aromatic and aliphatic dicarboxylic acids such as diallyl phthalate, diallyl malonate, and diallyl succinate; and other difunctional vinyl and allyl agents such as divinylsulfone and N,N'-diallylpiperazine; the trifunctional cross-linking agents for example, 1,1,1-trimethylolpropane trimethacrylate

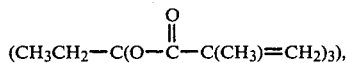

1,1,1-trimethylolpropane triacrylate, 1,1,1-trimethylolethane triacrylate, 1,1,1-trimethylolethane trimethacrylate, 1,3,5-triacryloylhexahydro-s-triazine, 1,3,5-trimethacryloylhexahydro-s-triazine, trivinylcyclohexane, and triallyl isocyanurate; and tetrafunctional cross-linking agents, for example, pentaerythritol tetramethacrylate, pentaerythritol tetramethacrylate, tetrallyloxyethane, and tetraallylpyromellitate.

A preferred cross-linking agent is divinylbenzene. Other preferred agents are methylenebisacrylamide and methylenebismethacrylamide represented respectively by the following formulas

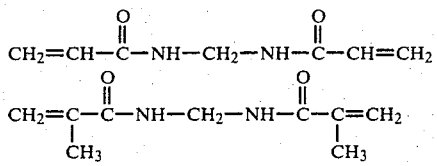

The vinylpyridine monomer can also be cross-linked with a divinylpyridine or a methylated divinylpyridine e.g. 2-methyl-4,6-divinylpyridine. It will be readily appreciated that other known or preparable cross-linking agents can be used to prepare the cross-linked polyvinylpyridine polymer used in the process of this invention.

Preferred cross-linked polymers of this invention are poly-(4-vinylpyridine)divinylbenzene (containing about 2 percent to about 5 percent cross-linking), poly-(4-vinylpyridine)-N,N'-methylenebisacrylamide and poly-(4-vinylpyridine)-N,N'-methylenebismethacrylamide.

The polyvinylpyridine polymers are prepared conveniently by heating the vinylpyridine in the presence of azobisisobutyronitrile and the cross-linking agent in aqueous solvent system. A suitable aqueous solvent system which can be used is saline solution and diisobutylketone. The saline solution promotes polymerization in the organic phase thus providing for a more complete polymerization.

The polymerization can also be carried out as described by Hallensleben and Wurm, *Angew. Chem. Int. Ed. Engl.* 15, 163 (1976) wherein the preparation of poly-(4-vinylpyridine)-divinylbenzene is described.

Alternatively the cross-linked polymers can be prepared in water via emulsion polymerization with surfactants such as polyvinyl alcohol or polyethylene oxide. Macroreticular beads of the cross-linked polymers can be prepared by procedures known in the art, for example, as described by U.S. Pat. No. 3,816,355.

The cross-linking agents described herein are commercially available compounds and can be prepared by known methods.

It will be appreciated by those practicing in the chemical arts that while the polymers formed with the different cross-linking agents are functional equivalents in the process, individual cross-linked polymers may have certain advantageous properties not shared by others. For example, certain of the polymers can be regenerated and reused numerous times while others withstand less regeneration and reuse.

Further, some of the cross-linked polymers are more readily washed free of impurities than others following their preparation. Likewise, some polymers are more costly than others. Also, with certain starting materials a lesser amount of one polymer may be required than with others.

The preferred extent of cross-linking in the polymer is between about 2% and about 5%. The desired range of cross-linking is obtained by using the appropriate amount of the cross-linking agent in the polymerization of the vinylpyridine. The polyvinylpyridine having the desired cross-linking rapidly absorbs the hydrogen chloride formed during the reaction of the penicillin sulfoxide with the N-chlorinating agent. Further, since the polymer is insoluble in the reaction medium, the acid is rapidly and completely removed from the reaction system. This rapid removal of the acid side product prevents its reaction with yet unreacted starting material and thus prevents competing reactions with the formation of undesired side products.

The cross-linked polyvinylpyridine can be used in a variety of forms. For example, it can be in the form of a fine powder or in the form of small beads, or in the form of macroporous beads. Preferably the form of the copolymer has a high surface area which is a measure of the availability of the basic sites of the polymer to the acid. Accordingly, the lower the average particle size of the polymer the higher will be the surface area and the greater availability of basic groups. Likewise, the copolymer in the form of macroporous beads has a high surface area including internal surface area with concomitant high exposure of the basic groups in the copolymer. For copolymer in the form of relatively uniform shape such as bead shaped, for example macroreticular beads, the preferred size is between about 20 microns and about 120 microns in diameter. For copolymer of irregular particle shape, such as may be obtained by crushing the copolymer resin in a hammer mill, the preferred particle size is obtained by collecting the particles passing through a sieve of about 120 mesh.

Copolymer having the cross-linking content of between about 1% and about 10% displays characteristic swelling in the organic solvents employed in the process. Copolymer having a higher cross-linking content swells to a lesser degree and, the extent of swelling decreases as the extent of cross-linking increases. The increased volume of the copolymer due to swelling allows for greatly enhanced access to the basic sites in the polymer by hydrogen chloride. Copolymers which are cross-linked to greater than 10% swell much less than those which are cross-linked to less than 10%, or within the preferred range, and although insoluble in the organic solvents are not efficient HCl binders.

The use of the cross-linked copolymer having the preferred particle size allows the process of this invention to be carried out at concentrations higher than those employed in the prior process wherein an alkylene oxide and calcium oxide are used as the acid binding agent (Ta-Sen Chou, U.S. Pat. No. 4,075,203). For example, at concentrations 3 or 4 fold greater than those permissible with the prior process, yields of product obtained are equal to or greater than those obtained in the prior process.

In carrying out the process of this invention, the N-chloro halogenating agent can be employed in molar excess with respect to the penicillin sulfoxide ester. However, between about 1 mole and about 1.5 moles of the N-chloro halogenating agent per mole of penicillin sulfoxide ester is generally employed. Preferably, the molar ratio of the N-chloro halogenating agent is between about 1.0 to about 1.1 to 1.5 moles per mole of penicillin sulfoxide.

The ratio of the amount of polymer employed per amount of penicillin sulfoxide ester is between about 1:1 and about 1:5 by weight. Preferably, the ratio is about 1:2 to about 1:3.

The highest yields of the intermediate 2-chlorosulfinylazetidinone-4-one obtained in the present process, as reflected by the yield of 3-exomethylenecepham sulfoxide obtained following the 2nd stage, are obtained when the concentration of the penicillin sulfoxide ester in an inert solvent is between about 20 mg./ml. to about 45 mg./ml. The penicillin sulfoxide has a low order of solubility in the inert aprotic solvents such as benzene and toluene and is somewhat more soluble in the halogenated hydrocarbon solvents which can be used. The 2-chlorosulfinylazetidinone product is, however, completely soluble in the inert solvents used in the process.

In one aspect of the improved process of this invention, the use of the cross-linked polymer having the preferred average particle size allows the first stage of the process to be carried out at higher concentrations of the penicillin sulfoxide. By employing the cross-linked polymer having the preferred particle size concentrations of penicillin sulfoxide ester of between about 50 mg./ml. and about 85 mg./ml. provide yields equal to the process when carried out at lower concentrations.

Penicillin sulfoxide esters which can be employed in the process of this invention are represented by the foregoing structural formula 1 wherein R is the residue of an organic carboxylic acid and wherein $R_1$ is a carboxylic acid protecting group. The term

of formula 1 can be any acyl group derived from a carboxylic acid which is stable under the conditions of the process of this invention as described herein. For example, the N-acyl group represented by the foregoing term in formula 1 can be any of the well recognized N-acyl groups employed in the preparation of cephalosporin antibiotics as described in the literature and which itself is not chlorinated with the N-chloro halogenating agent or which itself is not susceptible of reaction with the stannic chloride employed in the second stage of the process for preparing the 3-exomethylenecepham sulfoxide.

Penicillin sulfoxide esters which can be employed in the process of this invention are represented by the above formula 1 wherein R is hydrogen, $C_1$–$C_3$ alkyl, halomethyl or
cyanomethyl;
or R is the group R' wherein R' is phenyl or phenyl substituted by 1 or 2 substituents selected from the group consisting of $C_1$–$C_4$ alkyl, $C_1$–$C_4$ alkoxy, halo, protected hydroxy, nitro, cyano and trifluoromethyl;
or R is a group of the formula

wherein R" is t-butyl, 2,2,2-trichloroethyl, benzyl, 4-nitrobenzyl or 4-methoxybenzyl;
or R is a group of the formula

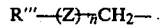

wherein R''' is R' as defined above, 2-thienyl, 3-thienyl, 2-furyl, 3-furyl or 1,4-cyclohexadienyl; n is 0 or 1, and Z is O or S, subject to the limitation that when n is 1, R''' is R';
or R is a substituted aralkyl group of the formula

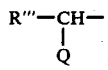

wherein R''' has the same meanings as defined above and Q is protected hydroxy or protected amino; and $R_1$ is a carboxylic acid protecting group.

In the above definition of the penicillin sulfoxides, the term "$C_1$–$C_3$ alkyl" refers to methyl, ethyl, n-propyl, and isopropyl; "halomethyl" refers to chloromethyl and bromomethyl.

Illustrative of the substituted phenyl groups represented by the term "R'" in the above formula are 4-methylphenyl, 3-ethylphenyl, 2,4-dimethylphenyl, 4-n-propylphenyl, 4-t-butylphenyl, 2-methoxyphenyl, 4-ethoxyphenyl, 3-isopropoxyphenyl, 4-isobutyloxyphenyl, 4-chlorophenyl, 3,4-dichlorophenyl, 3-chloro-4-fluorophenyl, 4-nitrophenyl, 2-cyanophenyl, 4-trifluoromethylphenyl, and like mono or di-substituted phenyl groups, and the phenyl groups substituted with protected hydroxy are illustrated by such groups as 3-formyloxyphenyl, 4-trityloxyphenyl, 4-benzyloxyphenyl, 3-nitrobenzyloxyphenyl, 4-chloroacetoxyphenyl, and like protected hydroxy-substituted phenyl groups.

Illustrative of the groups represented in the above definition by the term "R—$(Z)_n$—$CH_2$—" are phenoxymethyl, 4-fluorophenoxymethyl, 3-benzyloxyphenoxymethyl, 4-benzhydryloxyphenoxymethyl, 3-trityloxyphenoxymethyl, 4-nitrobenzyloxyphenoxymethyl, 4-trimethylsilyloxyphenoxymethyl, 3-nitrophenoxymethyl, 4-cyanophenoxymethyl, 4-trifluoromethylphenoxymethyl, 4-n-propylphenoxymethyl, 3-methoxyphenoxymethyl, 4-ethoxyphenoxymethyl, 3,4-dimethylphenoxymethyl, 3,4-dichlorophenoxymethyl, 2-fluorophenoxymethyl, phenylthiomethyl, 4-trimethylsilyloxyphenylthiomethyl, 3-nitrophenylthiomethyl, 4-cyanophenylthiomethyl, 4-trifluoromethylphenylthiomethyl, 2-chlorophenylthiomethyl, 3,4-dichlorophenylthiomethyl, 4-methylphenylthio, 3-methoxyphenylthiomethyl, 2,4-dimethylphenylthiomethyl, 4-benzhydryloxyphenylthiomethyl, 3-trityloxyphenylthiomethyl, 2-thienylmethyl, 3-thienylmethyl, 2-furylmethyl, and 3-furylmethyl.

Illustrative of the groups defined in the above formula wherein R is a substituted arylalkyl group of the formula R'''—CH—(Q)— are α-(benzhydryloxy)-thien-2-ylmethyl, α-(4-nitrobenzyloxy)-thien-2-ylmethyl-, α-(t-butyloxycarbamido)-thien-2-ylmethyl, α-formyloxybenzyl, α-benzyloxybenzyl, α-t-butyloxycarbamidobenzyl, α-(2,2,2-trichloroethoxycarbamido)-benzyl, α-(trimethylsilyloxy)-4-bromobenzyl, α-(benzhydryloxycarbamido)-3-chlorobenzyl, α-benzhydryloxy)-furan-2-ylmethyl, α-(t-butyloxycarbamido)-furan-2-ylmethyl, α-(4-nitrobenzyloxy)-2-cyanobenzyl, α-formyloxy-4-methylbenzyl, α-(benzyloxycarbamido)-4-methoxybenzyl, and α-(trimethylsilylamino)benzyl.

In the above formula, $R_1$ represents a carboxylic acid-protecting group. Such groups are those ester-forming groups commonly employed in the cephalosporin antibiotic art to block or protect the $C_4$ carboxylic acid function of a molecule while a reaction or sequence of reactions involving other sites in the molecule are carried out. These protecting groups are readily removed by cleavage under acidic hydrolysis conditions or under conditions of hydrogenolysis. Examples of such carboxylic acid-protecting ester groups are t-butyl, the haloalkyl ester groups such as the trihaloalkyl groups, for example 2,2,2-trichloroethyl and the monohaloalkyl groups such as 2-iodoethyl; the benzyl type ester protecting groups, for example benzyl, 4-methoxybenzyl, 4-nitrobenzyl, and 3,5-dimethoxybenzyl; the diarylalkyl protecting groups such as a diphenylmethyl and 4,4'-dimethoxydiphenylmethyl; and other recognized protecting groups, for example phenacyl, p-halophenacyl such as p-chlorophenacyl, and the succinimidomethyl ester forming group. The $R_1$ protecting groups function in the improved process of this invention merely as carboxylic acid-protecting groups and are not critical to the process. Other commonly recognized carboxylic acid-protecting groups can be employed, for example those described by E. Haslam in *Protective Groups in Organic Chemistry*, J. F. W. McOmie, ed., Plenum Press, N.Y., 1973, chapter 5. Preferred ester groups represented by the term $R_1$ in the process of this invention are t-butyl, diphenylmethyl, p-methoxybenzyl, and p-nitrobenzyl. The p-nitrobenzyl ester is an especially preferred carboxylic acid protecting group of this invention.

The term "protected-hydroxy" in the above formula refers to the commonly employed hydroxy-protecting groups which are readily removable. Such groups include, for example, the formyloxy group, acetoxy, chloroacetoxy, benzyloxy, p-nitrobenzyloxy, trityloxy, and the trimethylsilyloxy group. As with the above-described carboxylic acid protecting groups, the hydroxy-protecting groups function merely as blocking groups to avoid unnecessary side reactions during the process of this invention. Such groups are therefore not critical to avoid unnecessary side reactions during the process of this invention. Such groups are therefore not critical to the process of this invention and other groups in addition to those mentioned above would be recognized by those skilled in the art, for example those described by C. D. Reese in *Protecting Groups in Organic Chemistry*, supra, chapter 3.

The term "protected amino" employed in the above definition of the preferred starting materials in the present process refers to a substituted amine group wherein the substitutent is one of the commonly employed amino blocking or protecting groups used in the cephalosporin and penicillin arts. For example, the amino-protecting group is one which is readily removed following the process of this invention under conditions of acidic or basic hydrolysis or by hydrogenolysis. Examples of such groups include the groups forming urethanes with the amino group, for example the t-butyloxycarbonyl group, the benzyloxycarbonyl group, the substituted benzyloxycarbonyl group such as the p-methoxybenzyloxycarbonyl group, and the p-nitrobenzyloxycarbonyl group, the trihaloalkoxycarbonyl group such as 2,2,2-trichloroethoxycarbonyl group, the enamine-forming protecting groups such as the enamine formed with methyl or ethyl acetoacetate, and like recognized amino-protecting groups. Further examples of commonly employed amino-protecting groups are described by J. W. Barton in *Protective Groups in Organic Chemistry*, supra, chapter 2.

A preferred group of penicillin starting materials for use in the process of this invention are represented by formula I wherein R represents benzyl, phenoxymethyl, or 2-thienylmethyl and wherein $R_1$ represents a benzyl or a substituted benzyl group for example p-nitrobenzyl or p-methoxybenzyl.

The cross-linked polyvinylpyridine polymer functions uniquely in the process of this invention. The success of the reaction depends in part on the rapid removal of hydrogen chloride as it is generated. Even though the polymer is insoluble in the organic solvents employed, it rapidly takes up the hydrogen chloride, and, by virtue of its insolubility and swelling characteristics, effectively removes the acid from the reaction medium. Further, the copolymer is weakly basic and thus does not cause decomposition of the 2-chlorosulfinylazetidinone product which occurs with strongly basic hydrogen chloride acceptors.

The insolubility of the cross-linked copolymer described herein is one of its important features for another reason. Other weakly basic compounds commonly employed as acid scavengers which are at least partially soluble in the reaction medium are ineffective scavengers in the process of this invention. For example, little if any product is obtained when pyridine or quinoline are substituted for the alkylene oxide, or alkylene oxide-calcium oxide combination of the prior process. (T. S. Chou. U.S. Pat. No. 4,075,203) Further, the soluble polyvinylpyridine polymer which is not cross-linked is ineffective in the reaction.

The following Table I lists the yields of 3-exomethylenecepham-4-carboxylic acid ester sulfoxide obtained when the intermediate 2-chlorosulfinylazetidinone is prepared in the presence of poly-(4-vinylpyridine) having various percentages of cross-linking with a preferred cross-linking agent, divinylbenzene.

TABLE I

Effect of Cross-linking On Yield of 3-Exomethylenecepham Sulfoxide[1]

| Percent[2] Cross-linking | Polymer weight Penicillin weight | Percent Yield |
| --- | --- | --- |
| 2 | ½ | 59.5 |
| 2 | 2/5 | 43.4 |
| 3 | ½ | 63.5 |
| 4.5 | ½ | 63.3 |
| 30 | ½ | 0 |

[1]In each instance 50 g. of p-nitrobenzyl 6-phenoxy acetamido-2,2-dimethylpenam-3-carboxylate-1β-oxide were reacted with N-chlorophthalimide in the presence of the indicated ratio by weight of copolymer in 1800 ml. of toluene previously dried by azeotropic distillation. The unisolated 2-chlorosulfinyl azetidinone was converted with stannic chloride to the 3-exomethylenecepham sulfoxide.
[2]Poly(4-vinylpyridine)cross-linked with divinylbenzene.

As shown in Table I, when the extent of cross-linking is high, such as 30%, little if any yield of product is obtained. A high percentage of cross-linking decreases the extent to which the resin swells and thus renders the basic sites in the polymer less accessible to the hydrogen chloride.

As mentioned above the use of the cross-linked polyvinylpyridine polymer permits the preparation of 2-chlorosulfinylazetidinones at concentrations higher than those obtained under optimum conditions in the prior process. The cross-linked polymer in bead form having a particle size averaging between about 20 microns and about 120 microns in diameter, or that of particle size of about 120–140 mesh, is a preferred form of the polymer since it allows the process to be carried out with amounts of penicillin sulfoxide ester per volume of solvent three to four fold greater than those employable in the prior process. The higher concentrations thus allow a greater through-put in the two-step process to 3-exomethylenecepham sulfoxide ester. The high through-put realized is of significant economic value in the large-scale manufacturing process for the 3-exomethylenecepham sulfoxide ester.

The cross-linked polyvinylpyridine polymers can be regenerated with base and reused in the process of the invention. As noted above, after the process is completed the insoluble polymer is separated from the 2-chlorosulfinylazetidinone in solution. The polymer is boiled with acetone to remove any coprecipitated side-product, in particular, the insoluble imides and amides formed from the respective N-chloroimide or N-chloroamide chlorinating agents, and is then filtered. The polymer is then suspended in water and the pH of the suspension adjusted to between about pH 8 and pH 9.5 with a base such as 1 N sodium hydroxide. Once the pH remains stable the polymer is filtered, washed with water and acetone and is then dried, for example, under vacuum. Prior to resuse the regenerated polymer can be further dried by azeotropic distillation in a suitable solvent such as benzene or toluene.

Illustrative of the 2-chlorosulfinylazetidin-4-ones represented by the above formula 2 are the following:
benzyl 3-methyl-2-(2-chlorosulfinyl-4-oxo-3-phenylacetamido-1-azetidinyl)-3-butenoate,
p-nitrobenzyl 3-methyl-2-(2-chlorosulfinyl-4-oxo-3-phenylacetamido-1-azetidinyl)-3-butenoate,
2,2,2-trichloroethyl 3-methyl-2-(2-chlorosulfinyl-4-oxo-3-acetamido-1-azetidinyl)-3-butenoate,
p-methoxybenzyl 3-methyl-2-(2-chlorosulfinyl-4-oxo-3-butyramido-1-azetidinyl)-3-butenoate,
t-butyl 3-methyl-2-(2-chlorosulfinyl-4-oxo-3-benzamido-azetidinyl)-3-butenoate,
p-nitrobenzyl 3-methyl-2-[2-chlorosulfinyl-4-oxo-3-(2'-thienylacetamido)-1-azetidinyl]-3-butenoate,
p-nitrobenzyl 3-methyl-2-(2-chlorosulfinyl-4-oxo-3-phenoxyacetamido-1-azetidinyl)-3-butenoate,
p-nitrobenzyl 3-methyl-2-(2-chlorosulfinyl-4-oxo-3-phenoxyacetamido-1-azetidinyl)-3-butenoate,
2,2,2-trichloroethyl 3-methyl-2-(2-chlorosulfinyl-4-oxo-3-formamido-1-azetidinyl)-3-butenoate,
2,2,2-trichloroethyl 3-methyl-2-[2-chlorosulfinyl-4-oxo-3-(2'-thienylacetamido)-1-azetidinyl]-3-butenoate,
p-methoxybenzyl 3-methyl-2-(2-chlorosulfinyl-4-oxo-3-phenoxyacetamido-1-azetidinyl)-3-butenoate,
benzhydryl 3-methyl-2-(2-chlorosulfinyl-4-oxo-3-cyanoacetamido-1-azetidinyl)-3-butenate,
p-nitrobenzyl 3-methyl-2-(2-chlorosulfinyl-4-oxo-3-α-formyloxyphenylacetamido-1-azetidinyl)-3-butenoate,
p-nitrobenzyl 3-methyl-2-[2-chlorosulfinyl-4-oxo-3-(α-t-butyloxycarbonylaminophenylacetamido)-1-azetidinyl]-3-butenoate,
benzhydryl 3-methyl-2-[2-chlorosulfinyl-4-oxo-3-(α-t-butyloxycarbonylamino-1,4-cyclohexadienylacetamido)-1-azetidinyl]-3-butenoate,
t-butyl 3-methyl-2-[2-chlorosulfinyl-4-oxo-3-(4-chlorophenylthioacetamido)-1-azetidinyl]-3-butenoate, and
p-nitrobenzyl 3-methyl-2-[2-chlorosulfinyl-4-oxo-3-(3'-thienylacetamido)-1-azetidinyl]-3-butenoate.

The previously designated preferred penicillin sulfoxides afford the following preferred 2-chlorosulfinylazetidinones in the process of this invention where in formula 2 R is benzyl, phenoxymethyl or 2-thienylmethyl and $R_1$ is benzyl or a substituted benzyl group especially p-nitrobenzyl and p-methoxybenzyl.

In a preferred embodiment of the process of this invention p-nitrobenzyl 6-phenoxyacetamido-2,2-dimethylpenam-3-carboxylate 1-oxide is reacted in dry toluene at the reflux temperature with N-chlorophthalimide in the presence of poly(4-vinylpyridine)divinylbenzene copolymer cross-linked to between about 2 and about 5 percent. The heterogeneous reaction mixture is heated at the reflux temperature with stirring for about 1 hour and 40 minutes and is then cooled to a temperature of about 10° C. The cooled mixture is filtered to remove the insoluble copolymer and the filtrate containing the 2-chlorosulfinylazetidin-4-one is treated with stannic chloride to effect cyclization to the 3-exomethylenecepham sulfoxide ester as described hereinafter.

When the above embodiment of the process is carried out under elevated pressure, i.e. from about 5 psig to about 20 psig, the reaction temperature is increased to about 135° C. and the reaction time is decreased to about one third the time required at the reflux temperature at atmospheric pressure.

In another preferred embodiment of the invention p-nitrobenzyl 6-phenoxyacetamido-2,2-dimethylpenam-3-carboxylate-1-oxide is reacted in dry toluene at the reflux temperature with N-chlorophthalimide in the presence of poly(4-vinylpyridine)methylenebisacrylamide cross-linked to about 10 percent. The heterogeneous reaction mixture is heated at the reflux temperature with stirring for about two hours and is then cooled to about 15° C. The mixture is filtered to remove the polymer and phthalimide and the filtrate containing the azetidinone sulfinyl chloride is treated with stannic chloride to form the 3-exomethylenecepham sulfoxide ester as described hereinbelow. This embodiment of the process also can be carried out to advantage at elevated pressures.

As described above the 2-chlorosulfinylazetidinone produced in the process of this invention can be converted without isolation to a 3-exomethylenecepham sulfoxide ester in the process described by Kukolja in U.S. Pat. No. 4,052,387. In copending application Ser. No. 960,346 filed Nov. 13, 1978, now U.S. Pat. No. 4,190,724 there is disclosed an improved process for carrying out the cyclization to a 3-exomethylenecepham sulfoxide ester. The improved process is carried out as follows.

Following the reaction of the penicillin sulfoxide ester with the N-chloro halogenating agent in the presence of the cross-linked polyvinylpyridine to provide the 2-chlorosulfinylazetidinone, the insoluble polymer is separated from the reaction medium and, without isolation of the intermediate, the reaction medium is treated first with an oxo-ligand-forming compound as hereinafter defined and then with stannic chloride. Upon addition of the stannic chloride in the presence of the oxo-ligand-forming compound, a solid complex forms in the reaction medium. According to this improvement in the process, the insoluble complex formed with the sulfinyl chloride and the stannic chloride as described by Kukolja in U.S. Pat. No. 4,052,387 is stabilized by oxo ligands when formed in the presence of an oxo-ligand-forming compound. The stabilized complex is stirred for between about 3 hours and about 20 hours and is then separated from the reaction medium and washed with a hydrocarbon solvent. The complex is then slowly added to an hydroxy-containing compound for example, methanol or ethanol, to disrupt the complex and provide the 3-exomethylenecepham sulfoxide ester product.

Oxo-ligand-forming compounds which can be used in the process are alkyl and cycloalkyl ethers, for example, dimethyl ether, diethyl ether, di-n-propyl ether, di-n-butyl ether, and the like; cycloalkyl ethers, such as tetrahydrofuran and tetrahydropyran, and the like; ketones and cyclic ketones, such as acetone, diethyl ketone, methylethyl ketone, methyl n-propyl ketone, methyl isopropyl ketone, methyl isobutyl ketone, and the like; cyclic ketones, such as cyclobutanone, cyclopentanone, cyclohexanone, cycloheptanone, and the like, including the alkyl substituted cycloalkyl ketones, for example, the methyl substituted cyclohexanones and the methyl substituted cyclopentanones; trialkyl and triarylphosphine oxides, such as the tri-lower alkylphosphine oxides, for example, trimethylphosphine oxide, triethylphosphine oxide, tri-(n-propyl)phosphine oxide, tri-(n-butyl)phosphine oxide, and the like; tricycloalkylphosphine oxides, such as tricyclohexylphosphine oxide, and the like; triarylphosphine oxides, for example, triphenylphosphine oxide and the like.

The preferred oxo-ligand-forming compounds are diethyl ether, acetone and diethyl ketone.

As previously mentioned, the oxo-ligand-forming compound is preferably added to the solution of the 2-chlorosulfinylazetidin-4-one compound prior to the addition of the stannic chloride. Alternatively, the oxygen-ligand compound can be added with the stannic chloride.

Generally, the solution of the 2-chlorosulfinylazetidinone is cooled to a temperature of about 0° to about 15° C. prior to the addition of the oxo-ligand compound and the stannic chloride. Thereafter, the reaction is allowed to stir at room temperature for between about 3 and about 20 hours to ensure completion of the cyclization to the 3-exomethylenecepham sulfoxide ester. The 2-chlorosulfinylazetidinone-stannic chloride-oxo-ligand complex is then separated from the solution, for example, by filtration, centrifugation or other conventional means, and is washed with an inert hydrocarbon solvent, for example, pentane, hexane or toluene. The stable complex can be stored for later use or, preferably, it is next decomposed in the following manner. The solid complex is slowly added to an excess of an hydroxy-containing compound to provide the 3-exomethylenecepham sulfoxide ester. The lower alcohols, such as methanol and ethanol, are suitable hydroxy-containing compounds for the decomposition.

The structure of the 2-chlorosulfinylazetidinone-stannic chloride-oxo-ligand complex has not as yet been determined. However, it appears that one molecule of the oxo-ligand compound forms a co-ordinate bond with at least one central tin atom of the complex. It is to be noted that stannic chloride can possibly form a co-ordinate bond with the sulfinyl oxygen atom, as well as with the oxygen atoms of the amide function in the 3-position of the azetidinone and possibly with the carbonyl oxygen of the ester function.

The oxo-ligand compound is added in an amount corresponding to between about 1 and 2 moles per mole of 2-chlorosulfinylazetininone and preferably between about 0.8 and about 1.2 moles per mole, while the stannic chloride is employed in an amount corresponding to between about 2 and about 3 moles per mole of 2-chlorosulfinylazetidinone.

The 2-chlorosulfinylazetidinone-stannic chloride-oxo-ligand complex is usually highly colored and, depending upon the particular sulfinyl chloride employed in the process, can vary from red to orange-red to brown.

As previously mentioned, the oxo-ligand stabilized complex is more stable than the 2-chlorosulfinylazetidinone-stannic chloride complex formed in the prior process as described by Kukolja in U.S. Pat. No. 4,052,387. The oxygen-ligand, by virtue of forming a co-ordinate bond, renders the complex more stable thereby preventing deterioration of the complex prior to completion of the cyclization reaction to form the 3-exomethylenecepham sulfoxide ester. Accordingly, the oxygen-ligand complex of this invention affords higher yields of the product. Further, by virtue of the oxygen-ligand participation in the complex, the complex is generally obtained in solid form, whereas without the oxygen-ligand participation less pure complex formation is often obtained resulting in the complex being precipitated as a difficult to handle gum rather than as a solid material.

In practicing the improved process of this invention, certain penicillin sulfoxides are preferred as starting materials in that the resulting 3-exomethylenecepham sulfoxide ester products are preferred intermediates for the preparation of antibiotic compounds.

Examples of preferred starting materials are p-nitrobenzyl 6-phenoxyacetamido-2,2-dimethylpenam-3-carboxylate-1-oxide, p-nitrobenzyl 6-phenylacetamido-2,2- dimethylpenam-3-carboxylate-1-oxide, and p-nitrobenzyl 6-(2-thienylacetamido)-2,2-dimethylpenam-3-carboxylate-1-oxide.

Examples of the correspondingly substituted 2-chlorosulfinylazetidinones prepared in the process with the preferred penicillin sulfoxides are as follows.

p-nitrobenzyl 3-methyl-2-(2-chlorosulfinyl-4-oxo-3-phenoxyacetamido-1-azetidinyl)-3-butenoate, p-nitrobenzyl 3-methyl-2-(2-chlorosulfinyl-4-oxo-3-phenylacetamido-1-azetidinyl)-3-butenoate, and p-nitrobenzyl 3-methyl-2-[2-chlorosulfinyl-4-oxo-3-(2'-thienylacetamido)-1-azetidinyl]-3-butenoate.

Examples of the preferred 3-exomethylenecepham sulfoxide ester products prepared with the preferred penicillin sulfoxide esters are:

p-nitrobenzyl 7-phenoxyacetamido-3-exomethylenecepham-4-carboxylate-1-oxide, p-nitrobenzyl 7-phenylacetamido-3-exomethylenecepham-4-carboxylate-1-oxide, and p-nitrobenzyl 7-(2'-thienylacetamido)-3-exomethylenecepham-4-carboxylate-1-oxide.

As previously mentioned, in the starting penicillin sulfoxide ester the configuration of the sulfoxide can be either α or β or a mixture of the two configurations. The configuration of the sulfoxide in the 3-exomethylenecepham ester product is β.

An especially preferred embodiment of this invention is illustrated in the following reaction scheme wherein p-nitrobenzyl 6-phenoxyacetamido-2,2-dimethylpenam-3-carboxylate-1-oxide is reacted in essentially dry toluene with N-chlorophthalimide in the presence of poly(4-vinylpyridine) cross-linked to the extent of about 2% with divinylbenzene and having an average particle size of about 50 microns, to form the correspondingly substituted 2-chlorosulfinylazetidinone ester. The insoluble polymer and phthalimide are separated from the reaction medium and the filtrate is cooled. Approximately 1 molar equivalent of diethyl ether is added to the cooled filtrate followed by stannic chloride with formation of an orange-red complex containing the ether-ligand. Thereafter, the complex is stirred at room temperature for about 10 hours, is filtered, washed with hexane and added to a large excess of methyl alcohol to form a suspension of p-nitrobenzyl 7-phenoxyacetamido-3-exomethylenecepham-4-carboxylate-1β-oxide.

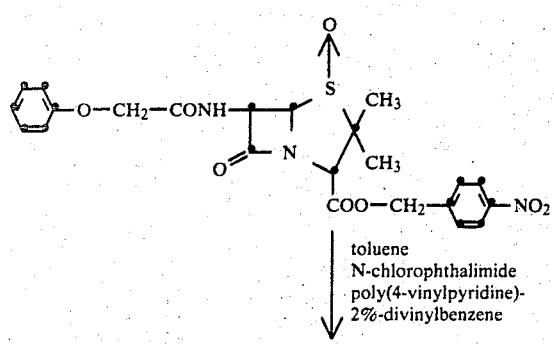

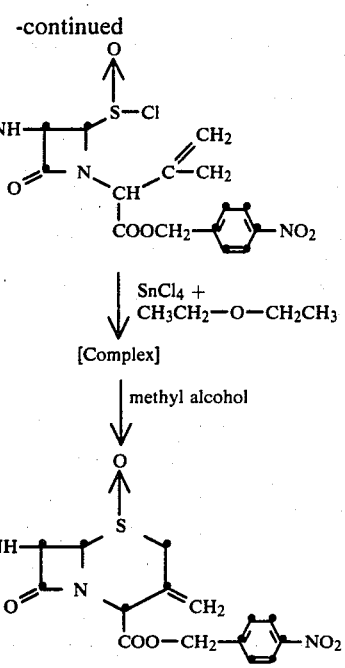

The following examples further illustrate the process of this invention. Unless specified otherwise, the penicillin sulfoxides have the β-configuration.

EXAMPLE 1

Preparation of poly(4-vinylpyridine)-divinylbenzene copolymer

To a 2-liter, 3-necked round bottom flask were added 1100 ml of water and 4.8 g. of poly(vinyl alcohol) and the solution was heated under nitrogen to 80° C. A solution of 50 g. of 4-vinylpyridine and 3.0 g. of divinylbenzene in 100 ml. of toluene was rapidly added with stirring to the hot solution, followed by the addition of 2 g. of azobisisobutyronitrile. The copolymer began to form at once and the suspension was stirred vigorously at 80° C. for about 16 hours.

The copolymer was collected by filtering the reaction mixture through cloth and was washed extensively with water, acetone, diethyl ether, methylene chloride and lastly with methyl alcohol. Swelling was encountered during the diethyl ether washing and with the methylene chloride and methyl alcohol washings. The copolymeric resin was then dried in vacuo to yield 45.05 g. of the dried resin.

The resin was finished by grinding and collecting the material which passed through 60 mesh sieve.

The nitrogen content of the resin was 12.35% as determined by combustion.

EXAMPLE 2

Two liters of reagent grade toluene were binary-distilled by removing and discarding 200 ml. of liquid through a Dean-Stark water trap. The heat was removed and 50 g. of 4-vinylpyridine-divinylbenzene copolymer (ca. 2% cross-linked) were added followed by 100.3 g. of p-nitrobenzyl 6-phenoxyacetamido-2,2-dimethylpenam-3-carboxylate-1-oxide and 38.4 g. of N-chlorophthalimide. The suspension was heated at the reflux temperature for 100 minutes and was then cooled to 10° C. and stirred for 10 minutes. The reaction suspension was filtered and the filtrate was cooled in an ice bath. Diethyl ether (18.28 ml.) was added to the cold filtrate followed by 50 ml. of stannic chloride. The light orange-red complex which formed was stirred 30 minutes at ice bath temperature and for about 16 hours at room temperature, was filtered and washed on the filter with 400 ml. of hexane. The complex was slowly added to 600 ml. of methyl alcohol with stirring. The suspension was stirred for 4 hours at a temperature of 0° C. The off-white precipitate of the product, p-nitrobenzyl 7-phenoxyacetamido-3-exomethylenecepham-4-carboxylate-1-oxide, was filtered, washed with 100 ml. of methyl alcohol, and dried in vacuum. The crystalline product, obtained in 76.2% yield, was off-white in color and melted at about 194.5° to about 195° C.

The preceding example illustrates the process carried out at the concentration of penicillin sulfoxide to solvent of about 50 g. to 1800 ml. which was the maximum concentration at which the prior art process afforded the best yield. The following examples in tabular form illustrate the process of the invention when carried out at three times the concentration used in Example 2 with copolymer having the preferred average particle size.

| Example No. | Pencillin (g) Toluene (ml.) | Particle[1] size ($\mu$) | Percent[2] Yield |
|---|---|---|---|
| 3 | 15/175 | 40 | 71.1 |
| 4 | 15/175 | 70 | 73.0 |
| 5 | 15/175 | 100 | 73.9 |

[1]Poly(4-vinylpyridine)-divinylbenzene in bead form.
[2]Percent yield of p-nitrobenzyl 7-phenoxyacetamido-3-exomethylenecepham-4-carboxylate-1-oxide.

EXAMPLE 6 p-Nitrobenzyl 7-(4-methylphenoxyacetamido)-3-exomethylenecepham-4-carboxylate-1-oxide Toluene, 80 ml., was binary distilled by removing 8 ml. of liquid through a Dean-Stark trap. The toluene was cooled and 0.67 g. of poly(4-vinylpyridine)-divinylbenzyl copolymer (approximately 2% cross-linked), 2 g. of p-nitrobenzyl 6-(4-methylphenoxyacetamido)-2,2-dimethylpenam-3-carboxylate-1-oxide, and 0.77 g. of N-chlorophthalimide were added. The mixture was heated at the reflux temperature for 100 minutes, was cooled in an ice bath and filtered to remove the copolymer and phthalimide. To the yellow filtrate 0.36 ml. of diethyl ether was added followed by the addition of 1.0 ml. of stannic chloride. The resulting tan colored complex was stirred for 1 hour at 0° C. and then overnight at room temperature and was filtered. The dark brown complex was added to methyl alcohol. The complex began to decompose on addition to methyl alcohol and a slurry of the insoluble product formed. The slurry was stirred for 4 hours at 0° C., was filtered, washed with methyl alcohol and dried in vacuo at room temperature to yield 0.61 g. of p-nitrobenzyl 7-(4-methylphenoxyacetamido)-3-exomethylenecepham-4-carboxylate-1-oxide melting at about 172°–174° C. The nuclear magnetic spectrum of the product run in DMSO-$d_6$ showed the following signals (delta): 2.23 (s, 3H, methyl of 4-methylbenzyl), 3.83 (q, 2H, J=4, 9 cps, $C_2$H), 4.53 (s, 2H, amide methylene), 5.05 (d, 1H, J=4.5 cps, $C_6$H), 5.28 (s, 2H, p-nitrobenzyl methylene), 5.37 (s, 1H, $C_4$-H), 5.50 and 5.70 (2s, 2H, =$CH_2$), 5.80 (q, 1H, J=4.5, 10 cps, $C_7$-H), 6.73 and 7.03 (2d, NH, J=9 cps, 4-methylbenzyl aromatic H) and 7.40 and 8.17 (2d, 4H, J=9 cps, p-nitrobenzyl aromatic H).

EXAMPLE 7 p-Nitrobenzyl 7-phenylacetamido-3-exomethylenecepham-4-carboxylate-1-oxide

Reagent grade toluene, 300 ml., was binary-distilled by removing and discarding 30 ml. of liquid through a Dean-Stark water trap. The heat was removed and 2.50 g. of vinylpyridine-divinylbenzene copolymer (ca. 2% cross-linked) were added. The polymer suspension was heated to the reflux temperature for a few minutes to remove any water. The heating was discontinued and 7.28 g. (0.015 M) of p-nitrobenzyl 6-phenylacetamido-2,2-dimethylpenam-3-carboxylate-1-oxide and 2.88 g. of N-chlorophthalimide were added. The mixture was then heated at the reflux temperature for 100 minutes and was then cooled to 10° C. and filtered into a round bottom 3-necked flask chilled in an ice bath. Diethyl ether, 1.37 ml. (0.013 M) and stannic chloride, 3.75 ml., 0.032 M were added to give a brown insoluble complex. The complex was stirred at ice-bath temperature for 30 minutes and then at room temperature for about 16 hours. The chocolate brown complex was filtered, washed with 60 ml. of hexane, and was then slowly added to 45 ml. of methyl alcohol to form a suspension of the product, p-nitrobenzyl 7-phenylacetamido-3-exomethylenecepham-4-carboxylate-1-oxide. The suspension of product was stirred at ice-bath temperature for 4 hours, was filtered, washed with 15 ml. of methyl alcohol, and dried under vacuum to give 4.3 g. (59.3% yield) of the dried product melting at about 208° C. to about 208.5° C. after recrystallization from acetone.

EXAMPLE 8

2,2,2-Trichloroethyl 7-phenoxyacetamido-3-exomethylenecepham-4-carboxylate-1-oxide Toluene, 800 ml. was binary distilled under a Dean-Stark water trap by removing 80 ml. of liquid from the trap. The heat was discontinued and 6.68 g. of poly(4-vinylpyridine)divinylbenzene containing about 2 percent cross-linking, 20 g. of 2,2,2-trichloroethyl 6-phenoxyacetamido-2,2-dimethylpenam-3-carboxylate-1-oxide, and 7.74 g. of N-chlorophthalimide were added to the hot toluene. The suspension was heated at the reflux temperature for 100 minutes and was then cooled in an ice bath for about 20 minutes. The cold suspension was filtered to remove the copolymer and phthalimide and the filtrate was cooled in an ice bath. Diethyl ether, 3.66 ml., was added to the cold filtrate and, with stirring, 10 ml. of stannic chloride were added. After stirring for about 1 hour the complex began to precipitate. The suspension of dark complex was stirred overnight at room temperature and was filtered and washed with 80 ml. of hexane. The resulting tan sand like complex was added to 120 ml. of methyl alcohol and the mixture cooled in an ice bath. When after stirring for about 4 hours no product precipitated, the volume of the methyl alcohol was reduced to ⅓ its original volume by evaporation. The concentrate was dissolved in ethyl acetate and the solution washed twice with 5% aqueous sodium bicarbonate and with water and was then dried over magnesium sulfate. The dried solution was evaporated to dryness yielding 15.62 g. of the crude product 2,2,2-trichloroethyl 7-phenoxyacetamido-3-exomethylenecepham-4-carboxylate-1-oxide as a brown foam.

The product was suspended in 60 ml. of methyl alcohol and the suspension was warmed to about 50° C. to obtain a solution. On cooling to room temperature the product crystallized. The crystalline precipitate was filtered and dried yielding 1.9 g. of the product melting at about 143.5°–144° C.

NMR(CDCl$_3$):
3.75 (q, 2H, J=4 and 18 cps, C$_2$H)
4.58 (s, 2H, phenoxyacetyl methylene)
4.83 (d, 2H, J=1.5 cps, trichloroethyl CH$_2$)
4.95 (d, 1H, J=4.5 cps, C$_6$H)
6.06 (q, 1H, J=4.5 and 11 cps, C$_7$H)
5.53 (s, 1H, C$_4$H)
5.42 and 5.87 (2s, =CH$_2$)
8.16 (d, 1H, J=11 cps, NH) and
6.83–7.50 (m, 5H, aromatic H) delta.

The following is an example of the process wherein a penicillin α-sulfoxide is used as the starting material.

EXAMPLE 9

One liter of reagent grade benzene was azetropically dried by removing and discarding 100 ml. of liquid through a Dean-Stark water trap during distillation. The heat was removed from the benzene and 16.7 g. of poly(4-vinylpyridine)divinylbenzene copolymer (approximately 2% cross-linked), 19.2 g. of N-chlorophthalimide and 50.12 g. of p-nitrobenzyl 6-phenoxyacetamido-2,2-dimethylpenam-3-carboxylate-1α-oxide were added. The mixture was heated at the reflux temperature for 120 minutes. The light yellow suspension was cooled to 10° C. and stirred for 10 minutes and was then filtered to remove the insoluble polymer and phthalimide. Diethyl ether, 9.14 ml., was added to the light yellow filtrate followed by the addition of 25 ml. of stannic chloride. The almost colorless complex was stirred 30 minutes at 0° C. and overnight at room temperature. The granular complex had turned a light orange and was filtered, washed with 200 ml. of hexane, and dried to a light colored, free flowing powder. The complex was slowly added to 300 ml. of methyl alcohol with the immediate formation of a thick suspension of the product, p-nitrobenzyl 7-phenoxyacetamido-3-exomethylenecepham-4-carboxylate-1β-oxide. The suspension was stirred for 4 hours at 0° C., was filtered, washed with 50 ml. methyl alcohol and dried in vacuo to give 39.9 g. (79.9% yield) of product as very fine crystals melting at about 197°–198° C.

The following is an example of the process wherein poly(4-vinylpyridine)-divinylbenzene of approximately 4.5% cross-linking is used.

EXAMPLE 10

Four liters of reagent grade toluene was dried by binary distillation for 3 hours with the removal of 400 ml. of toluene and water collected in a Dean-Stark trap. The distillation was discontinued and 50.0 g. of copolymer (approximately 4.5% crosslinked), 100.3 g. of p-nitrobenzyl 6-phenoxyacetamido-2,2-dimethylpenam-3-carboxylate-1-oxide, and 45.68 g. of N-chlorophthalimide were added. The mixture was heated at the reflux temperature for 100 minutes and was then cooled to 0° C. to 5° C. and filtered into 35 ml. of cold toluene containing 50 ml. of stannic chloride. The bright red-orange complex which formed was stirred overnight at room temperature without a change in color. The complex was filtered, washed with pentane, and then added to 500 ml. of methyl alcohol. The slurry of product which formed was stirred for 6.5 hours at about 0° to 5° C. The slurry was filtered and the product, p-nitrobenzyl 7-phenoxyacetamido-3-exomethylenecepham-4-carboxylate, was washed with diethyl ether and dried to give 63.2 g. (63.3% yield).

EXAMPLE 11

Regeneration of poly(4-vinylpyridine)-divinylbenzene copolymer

The copolymer-phthalimide mixture, recovered from a typical reaction wherein 35.1 g. of copolymer was used, was slurried in 500 ml. of acetone. The slurry was heated to the boiling point on the steam bath and filtered while hot. The phthalimide is soluble in the hot acetone and is separated in solution from the copolymer on filtration. The copolymer was then slurried in 200 ml. of water and the pH of the slurry adjusted to pH 9.5 with 1 N sodium hydroxide (about 42 ml. were required). The copolymer was filtered and was washed with water until the wash water was neutral pH. The copolymer was next washed with acetone to remove water and then dried in vacuo at 50° C. The dried regenerated copolymer weighed 34.3 g. representing a 97.7% recovery.

The following is an example of the process wherein regenerated copolymer, previously used 3 times and regenerated after each use by the method described by the previous example is employed.

EXAMPLE 12

Reagent grade toluene, 460 ml., was binary-distilled by removing 30 ml. of liquid in a Dean-Stark trap. The heat was removed from the toluene and 12.0 g. of the regenerated copolymer were added. The suspension was refluxed using a Dean-Stark trap to remove water and heating was discontinued. To the warm suspension were added 36.0 g. of p-nitrobenzyl 6-phenoxyacetamido-2,2-dimethylpenam-3-carboxylate-1-oxide and 13.8 g. of N-chlorophthalimide. The reaction mixture was heated at the reflux temperature with stirring for 100 minutes. The brown suspension was cooled to 10° C. and was filtered and the filtrate chilled in an ice bath. To the cold filtrate were added consecutively 6.6 ml. of diethyl ether and 18 ml. of stannic chloride. The dark orange complex which formed was stirred 30 minutes at ice bath temperature and then at room temperature for about 16 hours and was filtered and washed with 150 ml. of hexane. The washed complex was slowly added to 215 ml. of methyl alcohol with formation of a slurry of the product, p-nitrobenzyl 7-phenoxyacetamido-3-exomethylenecepham-4-carboxylate-1-oxide. The slurry was stirred for 4 hours at ice bath temperature, was filtered, washed with 50 ml. of methyl alcohol and dried in vacuo to yield 25.7 g. of off-white product melting at about 195° C.

EXAMPLE 13

Preparation of 4-vinylpyridine-N,N'-methylenebisacrylamide

To a one-liter, 3-neck round bottom flask equipped with a heating mantle, nitrogen bubbler, stirrer, thermometer and reflux condenser were added 200 ml of deionized water and 75 g of sodium chloride. The solution was stirred under nitrogen for 30 minutes at room temperature and a solution of 30.0 g of 4-vinylpyridine, 3.0 g of N,N'-methylenebisacrylamide and 0.2 g of azobisisobutyronitrile in 90 ml of diisobutylketone was added. The temperature of the reaction solution was increased to between about 65° C. and about 70° C. with rapid stirring (200 rpm). After about 30 minutes some precipitate formed.

The reaction mixture was stirred with heating for about 18 hours and the polymer which had precipitated was recovered and washed as follows. First the diisobutylketone was distilled off by azeotropic distillation using a Dean-Stark trap and after the mixture had cooled to room temperature, 500 ml methyl alcohol were added. The suspension was stirred vigorously for about 15 minutes to disperse the polymer and to break up any large particles. The suspension was poured into 500 ml of water and the pH adjusted to less than pH$_2$ with hydrochloric acid. The acidified suspension was stirred for 30 minutes and was then filtered on a Buchner funnel through cheese cloth. The polymer was washed with three one-liter portions of water and separated from the first and second washes by decantation. After the third wash and pH of the suspension was adjusted to pH 8.0 with 8.5 with ammonium hydroxide and the polymer filtered. The polymer was washed again with with three one-liter portions of water and the wash decanted. Finally the polymer was washed for 15 minutes with 500 ml of methyl alcohol filtered and dried.

By the following the polymerization conditions and by employing the same amounts of 4-vinylpyridine and azobisisobutyronitrile as described by Example 13, the following cross-linked poly(4-vinylpyridine)polymers (abbreviated PVP) were prepared with the indicated amount of the designated cross-linking agent.

13a PVP-1,1,1-trimethylolpropane trimethacrylate was prepared with 3.0 g of 1,1,1-trimethylolpropane trimethacrylate.

13b PVP-ethylene diacrylate was prepared with 1.5 g of ethylene diacrylate.

13c PVP-triethyleneglycol dimethacrylate was prepared with 1.5 g of triethyleneglycol dimethacrylate.

13d PVP-diallyl malonate was prepared with 1.5 g of diallyl malonate.

The cross-linked polymers employed in the process of this invention such as those described in Examples 13a–13d are thoroughly washed prior to use by following the washing procedure described by Example 13.

EXAMPLE 14

Process with poly-(4-vinylpyridine)-methylenebisacrylamide

To a 3-neck one-liter round bottom flask equipped with a stirrer, a Dean-Stark trap and a reflux condenser were added 250 ml of toluene and 6.3 g of poly-(4-vinylpyridine)-N,N'-methylenebisacrylamide,

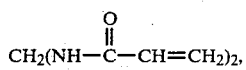

(10 percent cross-linked). The mixture was heated at the reflux temperature until all water was collected in the trap. Heating was discontinued and 18.79 g of p-nitrobenzyl 6-phenoxyacetamido-2,2-dimethylpenam-3-carboxylate-1-oxide and 8.48 g of N-chlorophthalimide were added rapidly to the hot mixture. Approximately 50 ml of dry toluene were used to rinse in the ester and chloro compound. The reaction mixture was then heated at the reflux temperature for 100 minutes and thereafter was cooled to a temperature between about 5° C. and about 10° C. The cold reaction mixture containing the chlorosulfinylazetidinone was filtered into a dry flask to separate the polymer and phthalimide and the filter cake was washed with dry toluene. The temperature of the cold filtrate containing the chlorosulfinyl compound was maintained at about 5° C. to about 10° C. and 3.43 ml of diethyl ether were added. Next, 9.38 ml of stannic chloride were added rapidly and the mixture was stirred in the cold for 30 minutes and for about 18 hours at room temperature. The reddish complex was filtered, pulled dry on the filter, washed with hexane, and dried. The dry solid complex was added to 113 ml of methyl alcohol and the suspension was stirred for 4 hours at ice bath temperature to obtain crystallization of the product. The suspension of the product was filtered and the product washed with methyl alcohol and dried. There were obtained 13.6 g of the product, p-nitrobenzyl 7-phenoxyacetamido-3-exomethylenecepham-4-carboxylate-1-oxide melting at about 193° C. to about 195° C. (72.5% yield). Purity of the product via HPLC was 92.5%.

EXAMPLE 15

Process with poly(4-vinylpyridine)-trimethylolpropane trimethylacrylate

The procedures and conditions described in the preceeding Example were repeated using the same amounts of solvent, starting material, chlorinating reagent, stannic chloride and diethyl ether except that 6.3 g of poly-(4-vinylpyridine)-trimethylolpropane trimethylacrylate,

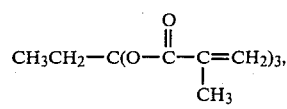

(3 percent cross-linked) were substituted for the poly(4-vinylpyridine)-methylenebisacrylamide. The stannic chloride complex was isolated and the product recovered by following the same procedures. There were obtained 12.44 g (63.3% yield) of p-nitrobenzyl 7-phenoxyacetamido-3-exomethylenecepham-4-carboxylate-1-oxide.

EXAMPLE 16

Process with poly-(4-vinylpyridine)-methyl-divinylpyridine

By following the reaction procedures and conditions described by Example 14, 500 ml. of toluene and 12.5 g of poly-(4-vinylpyridine)methyl-divinylpyridine (cross-linked to about two percent) were dryed by azeotropic distillation. p-nitrobenzyl 6-phenoxyacetamido-2,2-dimethylpenam-3-carboxylate-1-oxide, 37.5 g, and 16.95 g of N-chlorophthalimide were added to the dry mixture and the mixture was heated at the reflux temperature for 100 minutes to form the azetidinone sulfinyl chloride. The reaction mixture was filtered to remove the polymer and phthalimide and the filtrate treated with 18.75 ml of stannic chloride and 6.85 ml of diethyl ether. The complex which formed was stirred overnight at room temperature and was filtered and dried. The complex was decomposed in 225 ml of methyl alcohol and 23.0 g (61.33% yield) of p-nitrobenzyl 7-phenoxyacetamido-3-exomethylenecepham-4-carboxylate-1-oxide melting at about 191.5° C. to about 193.5° C. were obtained.

The cross-linked poly-(4-vinylpyridine)methyldivinylpyridine polymer employed in this Example was thoroughly washed prior to use by the washing procedure described by Example 13.

I claim:

1. In the process for preparing a 2-chlorosulfinylazetidin-4-one of the formula

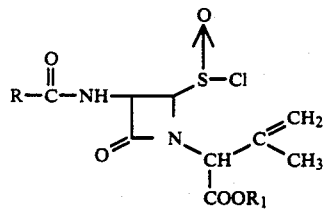

wherein

R is hydrogen, $C_1$-$C_3$ alkyl, halomethyl or cyanomethyl;

or R is the group R' wherein R' is phenyl or phenyl substituted by 1 or 2 substituents selected from the group consisting of $C_1$-$C_4$ alkyl, $C_1$-$C_4$ alkoxy, halo, protected hydroxy, nitro, cyano and trifluoromethyl; or R is a group of the formula

R''—O— wherein R'' is t-butyl, 2,2,2-trichloroethyl, benzyl, 4-nitrobenzyl or 4-methoxybenzyl; or R is a group of the formula R'''$(Z)_n$CH$_2$— wherein R''' is R' as defined above, 2-thienyl, 3-thienyl, 2-furyl, 3-furyl or 1,4-cyclohexadienyl; n is 0 or 1, and Z is O or S, subject to the limitation that when n is 1, R''' is R';

or R is a substituted aralkyl group of the formula

R'''—CH—
      |
      Q wherein R''' has the same meanings as defined above and Q is protected hydroxy or protected amino;

and $R_1$ is a carboxylic acid protecting group, which comprises heating in an inert organic solvent a penicillin sulfoxide ester of the formula

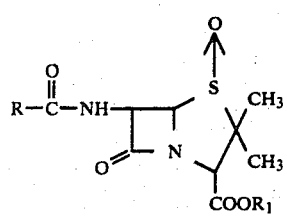

wherein R and $R_1$ are as defined above, at a temperature between about 75° C. and about 175° C. with an N-chlorohalogenating agent, the improvement which consists of heating said penicillin sulfoxide ester with the N-chlorohalogenating agent in the presence of an organic solvent insoluble, weakly basic cross-linked poly-4-(vinylpyridine) polymer in a ratio by weight of said polymer to penicillin sulfoxide of between about 1:1 and about 1:5, wherein said polymer is cross-linked to between about 1 percent and about 10 percent with a cross-linking agent selected from among the group consisting of divinylbenzene, N,N'-methylenebisacrylamide, N,N'-decamethylenebisacrylamide, N,N-diallylacrylamide, ethylene diacrylate, ethylene dimethacrylate, 1,1,1-trimethylolpropane trimethacrylate, 1,1,1-trimethylolpropane triacrylate, 1,1,1-trimethylolethane triacrylate, 1,1,1-trimethylolethane trimethacrylate, pentaerythritol tetramethacrylate, 1,3,5-triacryloylhexahydro-s-triazine, 1,3,5-trimethacryloylhexahydro-s-triazine, diallyl phthalate, diallyl malonate, diallyl succinate, N,N-diallylpiperazine, tetraallyloxyethane, tetraallylpyromellitate, trivinylcyclohexane, and divinylsulfone.

2. The process of claim 1 wherein the poly(4-vinylpyridine) is cross-linked with divinylbenzene, methylenebisacrylamide or methylenebismethacrylamide.

3. The process of claim 1 wherein R is a group of the formula R'''—Z)$_n$CH$_2$—.

4. The proces of claim 3 wherein R''' is phenyl or 2-thienyl.

5. The process of claim 1 wherein the N-chlorohalogenating agent is a compound of the formula

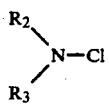

wherein $R_2$ is hydrogen, chloro, $C_1$-$C_3$ alkyl, cyclohexyl, phenyl, or phenyl substituted with chloro, bromo, methyl, or nitro, and $R_3$ is $R_4$—X— wherein $R_4$ is $C_1$-$C_3$ alkyl, cyclohexyl, phenyl, or phenyl substituted with chloro, bromo, methyl, or nitro, and X is $-\underset{\underset{Cl}{|}}{N}-\overset{O}{\underset{||}{C}}-$, $-\overset{O}{\underset{||}{C}}-$, $-O-\overset{O}{\underset{||}{C}}-$, or $-SO_2-$;

or $R_2$ and $R_3$ taken together with the nitrogen to which they are bonded define a heterocyclic structure of the formula

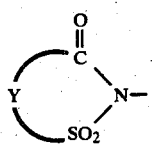

in which Y is o-phenylene or —(CH$_2$)$_n$— in which n is 2 or 3; or a structure of the formula

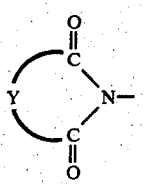

in which Y is as hereinbefore defined.

6. The process of claim 5 wherein the N-chlorohalogenating agent is a compound of the formula

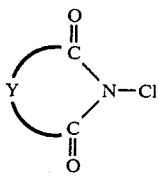

7. The process of claim 6 wherein the N-chlorohalogenating agent is N-chlorosuccinimide or N-chlorophthalimide.

8. The process of claim 6 wherein the N-chlorohalogenating agent is N-chlorophthalimide.

9. The process of claim 1 wherein the inert organic solvent is selected from the group consisting of benzene, toluene and xylene.

10. The process of claim 4 wherein the polymer contains between about 2 percent and about 5 percent cross-linking.

11. The process of claim 10 wherein the penicillin sulfoxide of the formula

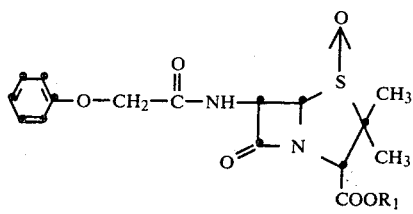

is reacted in toluene with N-chlorophthalimide in the presence of between about 1 mole and 1.5 mole of cross-linked polyvinylpyridine per mole of said penicillin sulfoxide ester.

12. The process of claim 11 wherein $R_1$ is t-butyl, diphenylmethyl, p-methoxybenzyl or p-nitrobenzyl.

13. The process of claim 11 wherein $R_1$ is p-nitrobenzyl.

14. The process of claim 11 wherein the cross-linked polyvinylpyridine is poly(4-vinylpyridine)-divinylbenzene, poly(4-vinylpyridine)methylenebisacrylamide or, poly(4-vinylpyridine)methylenebismethacrylamide.

15. The process of claim 11 wherein the process is carried out at a temperature between about 110° C. and about 155° C.

16. The process of claim 15 wherein the cross-linked polyvinylpyridine is poly(4-vinylpyridine)-divinylbenzene.

* * * * *